US012691230B2

(12) United States Patent
Rogers et al.

(10) Patent No.: US 12,691,230 B2
(45) Date of Patent: Jul. 28, 2026

(54) NEEDLE ASSEMBLY WITH EXTENDING SAFETY SHIELD

(71) Applicant: Kurin, Inc., San Diego, CA (US)

(72) Inventors: Bobby E. Rogers, Park City, UT (US);
Kevin Nason, Phoenix, AZ (US);
David Karl Stroup, San Diego, CA
(US)

(73) Assignee: KURIN, INC., San Diego, CA (US)

( * ) Notice: Subject to any disclaimer, the term of this
patent is extended or adjusted under 35
U.S.C. 154(b) by 964 days.

(21) Appl. No.: 17/962,487

(22) Filed: Oct. 8, 2022

(65) Prior Publication Data

US 2023/0109255 A1 Apr. 6, 2023

Related U.S. Application Data

(63) Continuation-in-part of application No. 16/045,321,
filed on Jul. 25, 2018, now Pat. No. 11,826,527.
(Continued)

(51) Int. Cl.
*A61M 5/32* (2006.01)
*A61M 25/06* (2006.01)

(52) U.S. Cl.
CPC ...... *A61M 5/3232* (2013.01); *A61M 25/0637*
(2013.01)

(58) Field of Classification Search
CPC .... A61M 5/3232; A61M 5/322; A61M 5/321;
A61M 5/3205; A61M 5/32;
(Continued)

(56) References Cited

U.S. PATENT DOCUMENTS

| | | | |
|---|---|---|---|
| 3,859,998 A | 1/1975 | Thomas | |
| 3,886,930 A | 6/1975 | Ryan | |

(Continued)

FOREIGN PATENT DOCUMENTS

| | | | |
|---|---|---|---|
| CN | 1404884 | 3/2003 | |
| CN | 1842353 | 10/2006 | |

(Continued)

OTHER PUBLICATIONS

U.S. Appl. No. 62/845,767, filed May 9, 2019, Brewer Michael.
(Continued)

*Primary Examiner* — Kevin C Sirmons
*Assistant Examiner* — Alexandra Lalonde
(74) *Attorney, Agent, or Firm* — Pillsbury Winthrop Shaw
Pittman, LLP

(57) ABSTRACT

A safety needle assembly includes a housing defining a
cavity and having a button, a hub positioned in the cavity,
and a needle connected with a distal face of the hub to extend
out of the housing. The assembly includes a shield posi-
tioned in the cavity having a retracted mode in which the
shield is retracted into the housing to expose the needle, and
a securement mode in which the shield is extended over a
distal end of the needle to cover the needle. A spring
connects between the hub and the shield and is configured to
transition the shield from the retracted mode to the secure-
ment mode. The assembly includes a lock-in mechanism
configured to releasably maintain the shield in the retracted
mode, and a lock-out mechanism configured to securely
maintain the shield in the securement mode.

20 Claims, 12 Drawing Sheets

Related U.S. Application Data

(60) Provisional application No. 63/254,046, filed on Oct. 8, 2021.

(58) Field of Classification Search
CPC .............. A61M 5/3257; A61M 5/3243; A61M 5/3271; A61M 5/3272; A61M 5/158; A61M 5/1626; A61M 5/326; A61M 5/3216; A61M 5/162; A61M 25/0637; A61M 25/0606; A61M 25/06; A61M 25/0631; A61M 25/0618; A61M 25/0612; A61M 25/0625; A61M 2005/3247; A61M 2005/3249; A61M 2005/3263; A61M 2005/3261; A61M 2005/325; A61M 2005/3264; A61M 2005/3252; A61M 2005/3254; A61M 2005/1585; A61M 2005/206; A61B 5/150656; A61B 5/15074; A61B 5/15003; A61B 5/150389
See application file for complete search history.

(56) References Cited

U.S. PATENT DOCUMENTS

| | | | |
|---|---|---|---|
| 4,207,870 A | 6/1980 | Eldridge | |
| 4,373,535 A | 2/1983 | Martell | |
| 4,690,154 A | 9/1987 | Woodford | |
| 5,097,842 A | 3/1992 | Bonn | |
| 5,147,329 A | 9/1992 | Brannon | |
| 5,518,005 A | 5/1996 | Brannon | |
| 5,658,259 A | 8/1997 | Pearson | |
| 5,865,803 A | 2/1999 | Major | |
| 5,873,841 A | 2/1999 | Brannon | |
| 6,013,037 A | 1/2000 | Brannon | |
| 6,540,732 B1 | 4/2003 | Botich | |
| 6,913,580 B2 | 7/2005 | Stone | |
| 7,727,198 B2* | 6/2010 | Nakajima | A61M 5/3257 |
| | | | 604/164.08 |
| 8,439,870 B2 | 5/2013 | Moyer | |
| 8,535,241 B2 | 9/2013 | Bullington | |
| 10,265,007 B2 | 4/2019 | Bullington | |
| 10,299,713 B2 | 5/2019 | Patton | |
| 10,596,315 B2 | 3/2020 | Bullington | |
| 10,624,977 B2 | 4/2020 | Bullington | |
| 10,881,343 B2 | 1/2021 | Bullington | |
| 11,213,232 B2 | 1/2022 | Ivosevic | |
| 11,234,626 B2 | 2/2022 | Bullington | |
| 11,259,727 B2 | 3/2022 | Bullington | |
| 11,395,612 B2 | 7/2022 | Bullington | |
| 11,419,531 B2 | 8/2022 | Bullington | |
| 11,439,332 B2 | 9/2022 | Bullington | |
| 11,589,843 B2 | 2/2023 | Bullington | |
| 11,612,340 B2 | 3/2023 | Bullington | |
| 11,653,863 B2 | 5/2023 | Bullington | |
| 11,660,030 B2 | 5/2023 | Bullington | |
| 11,737,693 B2 | 8/2023 | Bullington | |
| 11,786,155 B2 | 10/2023 | Bullington | |
| 11,789,017 B2 | 10/2023 | Bullington | |
| 2002/0103464 A1 | 8/2002 | Crawford | |
| 2005/0119627 A1 | 6/2005 | Crawford | |
| 2005/0273019 A1 | 12/2005 | Conway | |
| 2006/0189936 A1 | 8/2006 | Carlyon | |
| 2006/0276756 A1 | 12/2006 | Francavilla | |
| 2007/0066937 A1 | 3/2007 | Jones | |
| 2007/0185456 A1 | 8/2007 | Nakajima | |
| 2008/0114296 A1 | 5/2008 | Saulenas | |
| 2008/0167577 A1 | 7/2008 | Weilbacher | |
| 2008/0167619 A1 | 7/2008 | Tanaka | |
| 2008/0306452 A1* | 12/2008 | Crawford | A61M 5/3204 |
| | | | 604/110 |
| 2008/0319346 A1 | 12/2008 | Crawford | |
| 2009/0149812 A1 | 6/2009 | MacAulay | |
| 2009/0234322 A1 | 9/2009 | Fischer | |
| 2010/0063455 A1* | 3/2010 | Moyer | A61M 25/0637 |
| | | | 29/428 |
| 2010/0286611 A1* | 11/2010 | Schraga | A61M 5/3257 |
| | | | 604/110 |
| 2011/0071469 A1 | 3/2011 | Wilson | |
| 2011/0152755 A1 | 6/2011 | Schmalz | |
| 2011/0178473 A1* | 7/2011 | Richards | A61M 5/3257 |
| | | | 604/198 |
| 2012/0179119 A1* | 7/2012 | Ng | A61M 5/158 |
| | | | 604/263 |
| 2013/0189643 A1 | 7/2013 | Infanger | |
| 2015/0005666 A1 | 1/2015 | Terasawa | |
| 2015/0351678 A1 | 12/2015 | Bullington | |
| 2017/0181734 A1 | 6/2017 | Tzachar | |
| 2018/0140240 A1 | 5/2018 | Bullington | |
| 2018/0177445 A1 | 6/2018 | Rogers | |
| 2020/0289039 A1 | 9/2020 | Bullington | |
| 2021/0275068 A1 | 9/2021 | Miazga | |
| 2022/0151525 A1 | 5/2022 | Bullington | |
| 2022/0151527 A1 | 5/2022 | Bullington | |
| 2022/0160271 A1 | 5/2022 | Ivosevic | |
| 2022/0304600 A1 | 9/2022 | Hammer | |
| 2022/0304664 A1 | 9/2022 | Hammer | |

FOREIGN PATENT DOCUMENTS

| | | |
|---|---|---|
| CN | 106890384 A | 6/2017 |
| EP | 1221301 A2 | 7/2002 |
| EP | 1790374 A1 | 5/2007 |
| EP | 1985324 A1 | 10/2008 |
| JP | 2007143876 | 6/2007 |
| JP | 2008504934 | 2/2008 |
| WO | 2015118109 A1 | 8/2015 |

OTHER PUBLICATIONS

Office Action (Non-Final Rejection) dated Sep. 11, 2023 for U.S. Appl. No. 16/045,321, pp. 1-11.
Office Action (Non-Final Rejection) dated Apr. 6, 2023 for U.S. Appl. No. 16/045,321, pp. 1-15.
Office Action (Final Rejection) dated Apr. 20, 2022 for U.S. Appl. No. 16/045,321, pp. 1-34.
Office Action (Final Rejection) dated Jul. 20, 2021 for U.S. Appl. No. 16/045,321, pp. 1-32.
Office Action (Final Rejection) dated Dec. 15, 2020 for U.S. Appl. No. 16/045,321, pp. 1-26.
Office Action (Non-Final Rejection) dated Mar. 17, 2020 for U.S. Appl. No. 16/045,321, pp. 1-29.
Advisory Action dated Jul. 27, 2022 for U.S. Appl. No. 16/045,321, pp. 1-3.
Advisory Action dated Apr. 27, 2021 for U.S. Appl. No. 16/045,321, pp. 1-3.
Advisory Action dated Mar. 10, 2021 for U.S. Appl. No. 16/045,321, pp. 1-3.
Notice of Allowance mailed Oct. 2, 2023; pp. 1-7.
China National Intellectual Property Administration; First Office Action for CN 201880050411.8, mailed Jun. 30, 2021, 14 pages.
European Patent Office; International Search Report and Written Opinion PCT/US2018/043731; dated Oct. 30, 2018; 12pages.
*Retractable Techs., Inc.* v. *Becton Dickinson & Co.*, CA No. 2:07-CV-250, Claim Construction Order (E.D. Tex., Jan. 20, 2009). 20 pages.
Hillyer, Christopher D., et al. "Bacterial Contamination of Blodd Components: Risks, Strategies and Regulation," Hematology, 2003, pp. 575-589.
De Korte, Dirk, et al. "Diversion of first blood volume results in a reduction of bacterial contamination for whole-blood collections." Vox sanguinis 83.1 (2002): 13-16.
Brecher, Mark E., et al. "Bacterial contamination of blood components." Clinical microbiology reviews 18.1 (2005): 195-204.
Van Zundert, Adrien. "New closed IV catheter system." Acta Anaesthesiologica Belgica 56.3 (2005): 283-285.
Hall, Keri K., et al. "Updated review of blood culture contamination." Clinical microbiology reviews 19.4 (2006): 788-802.
Li, Yiwen, et al. "Direct labeling and visualization of blood vessels with lipophilic carbocyanine dye DiI." Nature protocols 3.11 (2008): 1703-1708.

(56)     References Cited

OTHER PUBLICATIONS

Page, Catherine, et al. "Blood conservation devices in critical care: a narrative review." Annals of intensive care 3 (2013): 1-6.

Abbott Point of Care, Cartridge and Test Information, Art: 714258-010; Rev. Date: Aug. 15, 2016, 1-6 pages.

Zimmon, David S. et al. "Effect of portal venous blood flow diversion on portal pressure." The Journal of Clinical Investigation 65.6 (1980): 1388-1397.

Patton, Richard G., et al. "Innovation for reducing blood culture contamination: initial specimen diversion technique." Journal of clinical microbiology 48.12 (2010): 4501-4503.

Tang, Menglin, et al. "Closed blood conservation device for reducing catheter-related infections in children after cardiac surgery." Critical Care Nurse 34.5 (2014): 53-60.

Ernst, Dennis J. et al. "NCCLS simplifies the order of draw: a brief history." MLO: medical laboratory observer 36.5 (2004): 1-5 pages.

Gottlieb, T. "Hazards of bacterial contamination of blood products." Anaesthesia and intensive care 21.1 (1993): 20-23.

Norberg, Alonna, et al. "Contamination rates of blood cultures obtained by dedicated phlebotomy vs intravenous catheter." Jama 289.6 (2003): 726-729.

Quilici, Nathalie, et al. "Differential quantitative blood cultures in the diagnosis of catheter-related sepsis in intensive care units." Clinical infectious diseases 25.5 (1997): 1066-1070.

Napolitano, Marcello, et al. "Quality control of bacterial contamination of blood components: the feasibility of diversion system testing." Blood Transfus 2 (2004): 231-232.

De Korte, Dirk, et al. "Effects of skin disinfection method, deviation bag, and bacterial screening on clinical safety of platelet transfusions in the Netherlands." Transfusion 46.3 (2006): 476-485.

Liumbruno, Giancarlo Maria, et al. "Reduction of the risk of bacterial contamination of blood components through diversion of the first part of the donation of blood and blood components." Blood Transfusion 7.2 (2009): 86.

NCCLS. Procedures for the Collection of Diagnostic Blood Specimens by Venipuncture; Approved Standard—Fifth Edition. H3-A5, vol. 23, No. 32. Replaces H3-A4; vol. 18, No. 7. 1-52 pages. http://demo.nextlab.ir/Organization/Documents/CLSI-Standards/CLSI-H3-A5.aspx.

Challiner, A., et al. "Venous/arterial blood management protection system." Anaesthesia 47.2 (1992): 169-169.

Murphy, Michael F. "Better Blood Transfusion." Journal of the Intensive Care Society 4.3 (2003): 78-80.

Palavecino, Elizabeth L., et al. "Detecting bacterial contamination in platelet products." Clinical laboratory 52.9-10 (2006): 443-456.

Sheppard, Chelsea A., et al. "Bacterial contamination of platelets for transfusion: recent advances and issues." Laboratory Medicine 36.12 (2005): 767-770.

Shulman, Gerald. "Quality of processed blood for autotransfusion." Journal of Extracorporeal Technology 32.1 (2000): 11-19.

Weinbaum, Fredric I., et al. "Doing it right the first time: quality improvement and the contaminant blood culture." Journal of Clinical Microbiology 35.3 (1997): 563-565.

Weinstein, Melvin P. "Blood culture contamination: persisting problems and partial progress." Journal of clinical microbiology 41.6 (2003): 2275-2278.

Weinstein, Melvin P., et al. "The clinical significance of positive blood cultures in the 1990s: a prospective comprehensive evaluation of the microbiology, epidemiology, and outcome of bacteremia and fungemia in adults." Clinical Infectious Diseases 24.4 (1997): 584-602.

Weinstein, Melvin P. "Current blood culture methods and systems: clinical concepts, technology, and interpretation of results." Clinical infectious diseases 23.1 (1996): 40-46.

Closed IV, BD Saf-T-Intima. "Catheter System, Becton, Dickinson and Company, Brochure." Retrieved from the Internet (Aug. 23, 2019). 4 pages.

Perez, P., et al. "Multivariate analysis of determinants of bacterial contamination of whole-blood donations." Vox Sanguinis 82.2 (2002): 55-60.

McDonald, Carl P. "Interventions implemented to reduce the risk of transmission of bacteria by transfusion in the English National Blood Service." Transfusion Medicine and Hemotherapy 38.4 (2011): 255-258.

Lifesciences, Edwards. "Conservation. Safety. Simplicity. Edwards Vamp and Vamp Jr. Systems." (2002). 4 pages.

Sheppard, et al., Bacterial Contamination of Platelets for Transfusion: Recent Advances and Issues, Labmedicine, vol. 36, No. 12, Dec. 2005 ("Sheppard 2005").

* cited by examiner

200

NEEDLE ASSEMBLY WITH EXTENDING SAFETY SHIELD

CROSS-REFERENCE TO RELATED APPLICATIONS

This Application claims the benefit of priority of U.S. Provisional Application 63/254,046, filed on Oct. 8, 2021, and also is a continuation-in-part of U.S. Non-Provisional application Ser. No. 16/045,321 (now U.S. Pat. No. 11,826, 257), filed on Jul. 25, 2018. Each of these applications is incorporated herein by reference in its entirety.

BACKGROUND

Intravenous access by a needle is performed in a medical setting for collecting bodily fluids such as blood from a patient, and infusing liquids into a patient. These procedures are usually performed using what are known as fluid collection sets and intravenous infusion sets. Such sets typically include flexible plastic tubing with a proximal end connected to a port and a distal end connected to a needle assembly.

Conventional needle assemblies include a hub and a needle cannula. Most needle assemblies further include a pair of flexible wings extending out from the hub or from near the hub, which can be folded toward each other to form a convenient handle for gripping by a technician to guide and manipulate the needle cannula. The wings can also be extended outward and laid flat for being taped to a skin surface area of a patient to secure the needle cannula in a desired position, i.e. after venipuncture.

One problem with the use of most conventional needle assemblies is inadvertent or accidental skin punctures with the needle, also called "sticks," particularly after patient venipuncture and use. Accidental sticks can be painful, and even dangerous by transmitting disease or pathogens from the patient to another person such as the technician. Accordingly, some needle assemblies currently on the market employ a retractable needle, i.e. a system where the needle is retracted or pulled back into a housing by a force, such as from a spring. Once retracted the needle is supposed to be permanently locked within the housing.

However, several problems exist with a current retractable needle assemblies. One problem is premature or inadvertent retraction, where a technician accidentally presses an actuator such as a button to retract the needle, especially before desired. This problem can occur even when the needle is inserted into a patient's vein, in which such retraction can be painful and often damages the vein or surrounding tissue.

Further, retraction of the needle, whether intentional or accidental, causes a rapid movement of the needle relative to a hub or housing, and any blood within the needle is no longer housed and can become aerosolized to be breathed in and or splattered onto surrounding surfaces, such as the patient, the technician, the patient's chair, etc.

Several problems exist with safety needle assemblies with one or more telescoping shields. First, once the shield is deployed, it needs to secured and locked into an extended position that completely covers the needle. Otherwise, if the needle still protrudes from the shield, or if the shield can be easily retracted back to the housing or hub, the safety feature is defeated. In either case, the deployment of a non-locking shield or non-completely-covering shield can provide a false sense of security to a technician or anyone else that might handle the needle assembly.

Further, conventional attempts to provide an effective telescoping shield for a safety needle assembly are either too complex, require too many parts and materials, and therefore are subject to multiple points of failure or high costs of manufacture.

What is needed is a safety needle assembly that does not utilize a retractable needle, which is simple and low-cost to make, and which effectively isolates a practitioner, patient, or any other person that handles the needle assembly, from an accidental or inadvertent needle stick, and form aerosolized or splattering blood.

SUMMARY

This document describes a safety needle assembly that provides a deployable shield to cover a needle after use, where the needle is fixed relative to a hub and housing, and which does not utilize a retractable needle (and experience the myriad problems associated with a retractable needle, as described above). The shield, once deployed to extend and cover the needle, is locked securely in place, given a lock-out latch that abuts a corresponding locking face, as is described in further detail below. The needle assembly disclosed herein is simple and low-cost to make, and once in the safety position or mode, effectively protects a practitioner, patient, or any other person that handles the needle assembly, from an accidental or inadvertent needle stick.

In some aspects, a safety needle assembly includes a housing having a proximal end, a distal end, and a side wall therebetween that defines an inner cavity, the housing including lock-in surface and a button formed in a top of the side wall proximate the lock-in surface, the button being depressible into the inner cavity of the housing, the housing further including a lock-out latch formed in a bottom of the side wall, the lock-out latch extending toward or into the inner cavity of the housing and having a forward locking face formed on a flexible arm. The safety needle assembly further includes a hub fixed with the proximal end of the housing, the hub being connected with a flexible outer tube extending outside the housing from hub, and being connected with an inner side of the hub. The safety needle assembly further includes a needle connected with the inner tube to extend at least partially from the distal end of the housing in a fixed position relative to the housing. The safety needle assembly further includes a spring having a first end and a second end, the first end abutting a forward abutment region of the hub.

In some aspects, the safety needle assembly further includes a shield provided in the inner cavity of the housing and having an abutment member for abutting the second end of the spring, the shield having a securement latch formed in a top of the shield, the securement latch being configured to latch with, connect to, or abut the lock-in latch of the housing in a first mode and to disengage with the lock-in latch upon depressing of the housing button in a deployment mode, the shield further having a bottom groove to bend away the flexible arm of the housing to clear the shield and to return the flexible arm such that the forward locking face of the lock-out latch engages a proximal end of the shield to inhibit retraction of the shield.

In some aspects, a safety needle assembly includes a housing defining a cavity and having a depressible button, a hub positioned in the cavity at a proximal end of the housing, and a needle connected with a distal face of the hub to extend out of a distal end of the housing. The safety needle assembly further includes a shield positioned in the cavity and around the needle. The shield has a retracted mode in which the shield is retracted into the housing to expose the needle out of the distal end of the housing, and a securement mode in which the shield is extended over a distal end of the needle to cover the needle. The safety needle assembly further includes a spring connected between the hub and the shield and configured to transition the shield from the retracted mode to the securement mode.

The safety needle assembly further includes a lock-in mechanism configured to releasably maintain the shield in the retracted mode. The lock-in mechanism includes a lock-in latch formed in the housing proximate the depressible button and having a rearward locking face that extends into the cavity, and a securement latch formed on the shield and configured to latch with the lock-in latch in the first mode, when the depressible button is depressed the securement latch is unlatched from lock-in latch to activate the spring to extend the shield to transition the shield from the retracted mode to the securement mode.

The safety needle assembly further includes a lock-out mechanism configured to securely maintain the shield in the securement mode. The lock-out mechanism includes a lock-out latch extending into the cavity from a flexible arm formed in the housing, the lock-out latch configured to abut a proximal end of the shield when the shield is deployed in the securement mode.

The details of one or more embodiments are set forth in the accompanying drawings and the description below. Other features and advantages will be apparent from the description and drawings, and from the claims.

BRIEF DESCRIPTION OF THE DRAWINGS

These and other aspects will now be described in detail with reference to the following drawings.

Like reference symbols in the various drawings indicate like elements.

DETAILED DESCRIPTION

This document describes a safety needle assembly for intravenous access and including a safety feature that solves many of the problems of conventional needle assemblies. The needle assembly includes a shield that can be activated and deployed, after intravenous access, to cover the needle, and locked in the deployed position to shield the needle from inadvertent needle sticks. The needle assembly includes an actuator that is optimally located on the needle assembly to allow one-handed operation of the needle assembly, while being configured to limit or avoid inadvertent activation of the actuator and deployment of the needle safety shield during use or venipuncture, by its size and/or position on the needle assembly, and by a predetermined threshold amount of force in pounds per square inch required to activate the actuator.

Figure 1:
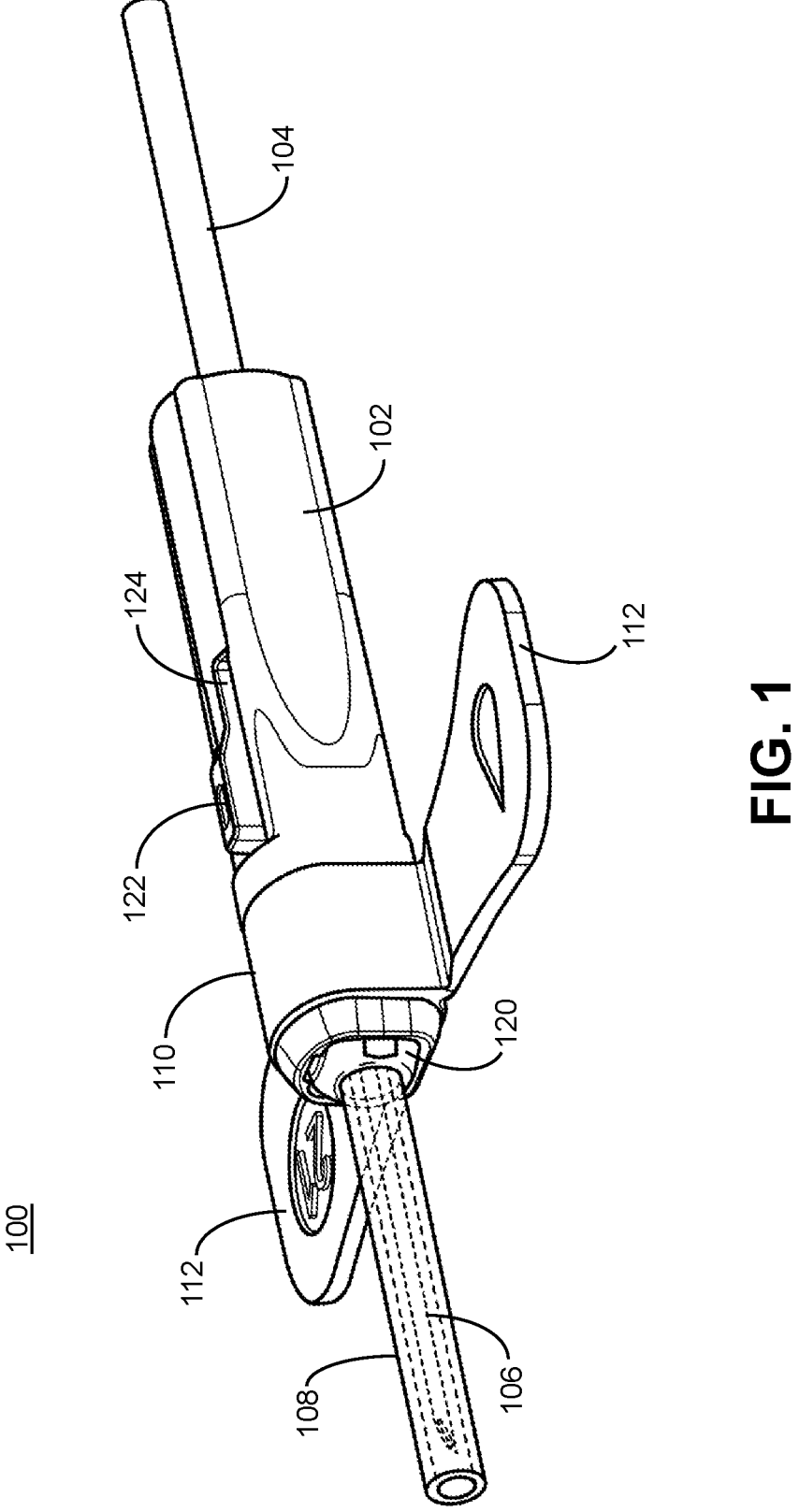
FIG. 1 illustrates a safety needle assembly in accordance with implementations described herein.

As shown generally in FIG. 1, a safety needle assembly 100 includes a housing 102 that houses a hub (not shown) that is fixed within the housing 102, and to which tubing 104 or a cannula is connected. The tubing 104 is connected at a proximal end by a fluid collection device, and/or a primary sample sidelining device such as that disclosed in U.S. patents application Ser. No. 15/140,443 (now U.S. Pat. No. 9,820,682), Ser. No. 15/855,439 (now U.S. Pat. No. 11,311, 219), Ser. No. 15/893,518 (now U.S. Pat. No. 10,827,964), Ser. No. 16/838,017 (now U.S. Pat. No. 12,373,174) and Ser. No. 17/336,178, for example, the contents of all which are incorporated herein by reference for all purposes. The tubing is configured to convey fluids such as blood from the safety needle assembly 100 to the external fluid collection device (not shown).

The hub within the housing 102 also supports, in a fixed location relative to the housing, a needle 106. When the safety needle assembly 100 is packaged and delivered, the needle 106 can be covered by a removable safety cover 108, such as a piece of semi-rigid tubing, for example, which can be removed by a technician during use, but which also protects the technician and others from an accidental needle stick before use.

The safety needle assembly 100 also includes a control portion 110 for controlling operations of the safety needle assembly 100, and which can include an cuff that at least partially circumscribes the housing 102 and one or more laterally-extending wings 112 extending from the cuff and laterally from the housing 102. The cuff of the control portion 110 can be seated in a groof, channel, or cut-in formed on the housing 102, preferably toward the distal end of the housing 102.

Each wing 112 can be grasped by a technician to manipulate and guide the safety needle assembly 100, and specifically the needle 106. The wings 112 and control portion 110 can be formed of an elastomeric material, such as a rubber or plastic, which provides the wings 112 in a permanent laterally-extended position unless grasped and manipulated by the technician to a different orientation or position. In their original, default orientation, the wings 112 can also provide a base by which the safety needle assembly 100, and thereby the needle 106, can be secured on or in a patient, respectively. For example, one or more of the wings 112 can be taped to a patient's skin proximate the venipuncture of the needle 106, to secure the needle 106 in the venipuncture.

In accordance with preferred implementations of the subject matter described, the safety needle assembly 100 includes a shield 120 that is originally retracted and locked within the housing 102 by a shield latch (not shown), but which is released and deployable for being extended completely over the needle 106 by depression of a button 122 by the technician, which releases the shield latch and allows a spring (not shown) to deploy the shield 120. The button 122 can be formed of a cut-out 124 of the housing 102, and can include a step or other heightened region for being conveniently depressed by a technician. The cut-out 124 can surround the button 122 on up to three sides, and can be configured to require a predetermined force to depress the button 122. Once deployed and extended, the shield is locked into a safety position (i.e. completely covering the needle 106) by a lock-out latch (not shown), all of which is described in further detail below.

The shield, once deployed to extend and cover the needle 106, the shield 120 is secured in place by the lock-out latch that abuts a corresponding locking face in the housing 102, as is described in further detail below. The safety needle assembly disclosed 100 disclosed herein is simple and low-cost to make, and effectively protects a technician, patient, or any other person that handles the safety needle assembly 100 from an accidental or inadvertent needle stick before and after venipuncture.

Figures 2A, 2B:
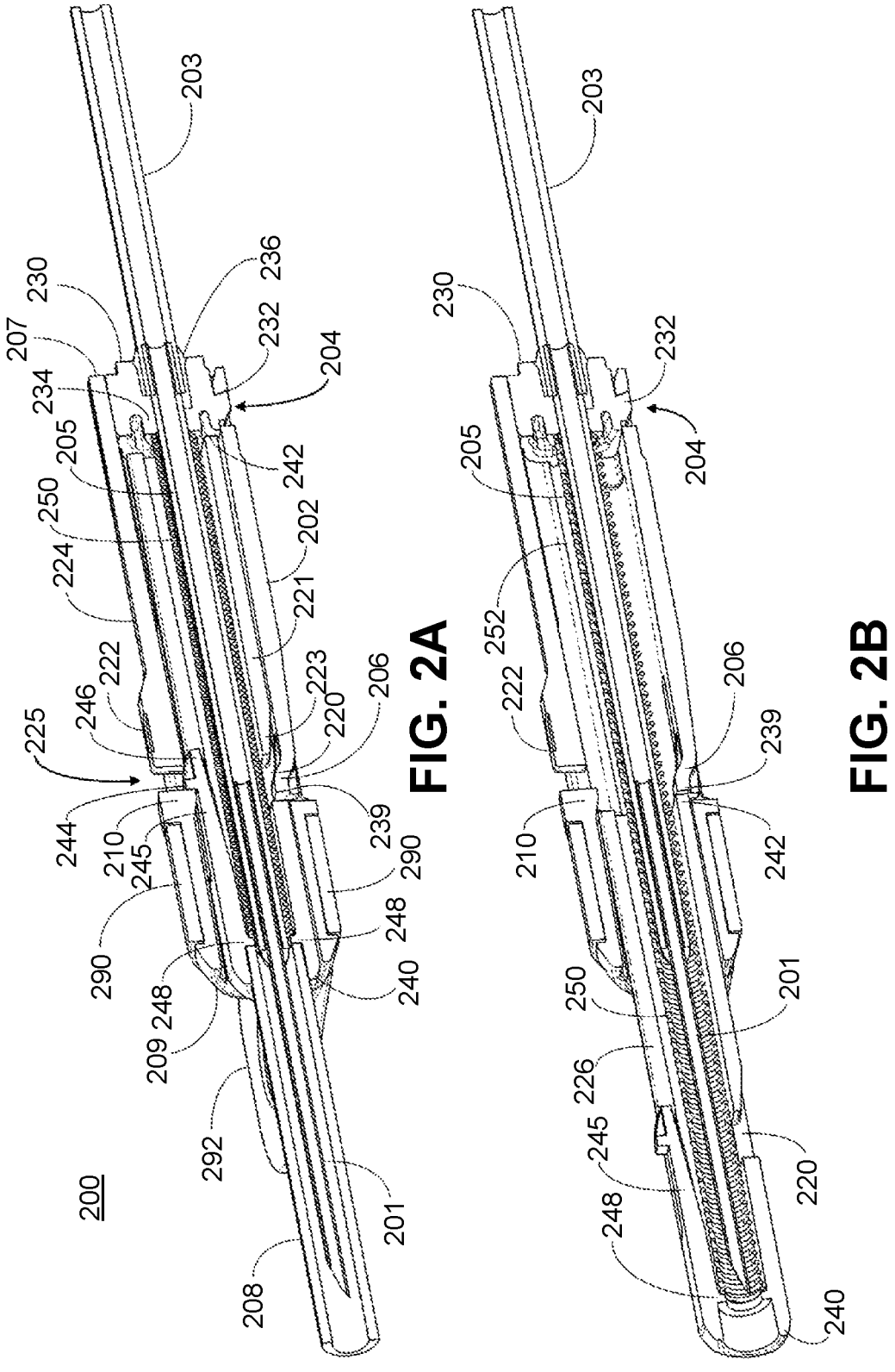
FIGS. 2A-2D illustrate a safety needle assembly in various modes, in accordance with the implementations described herein.
Figures 2C, 2D:
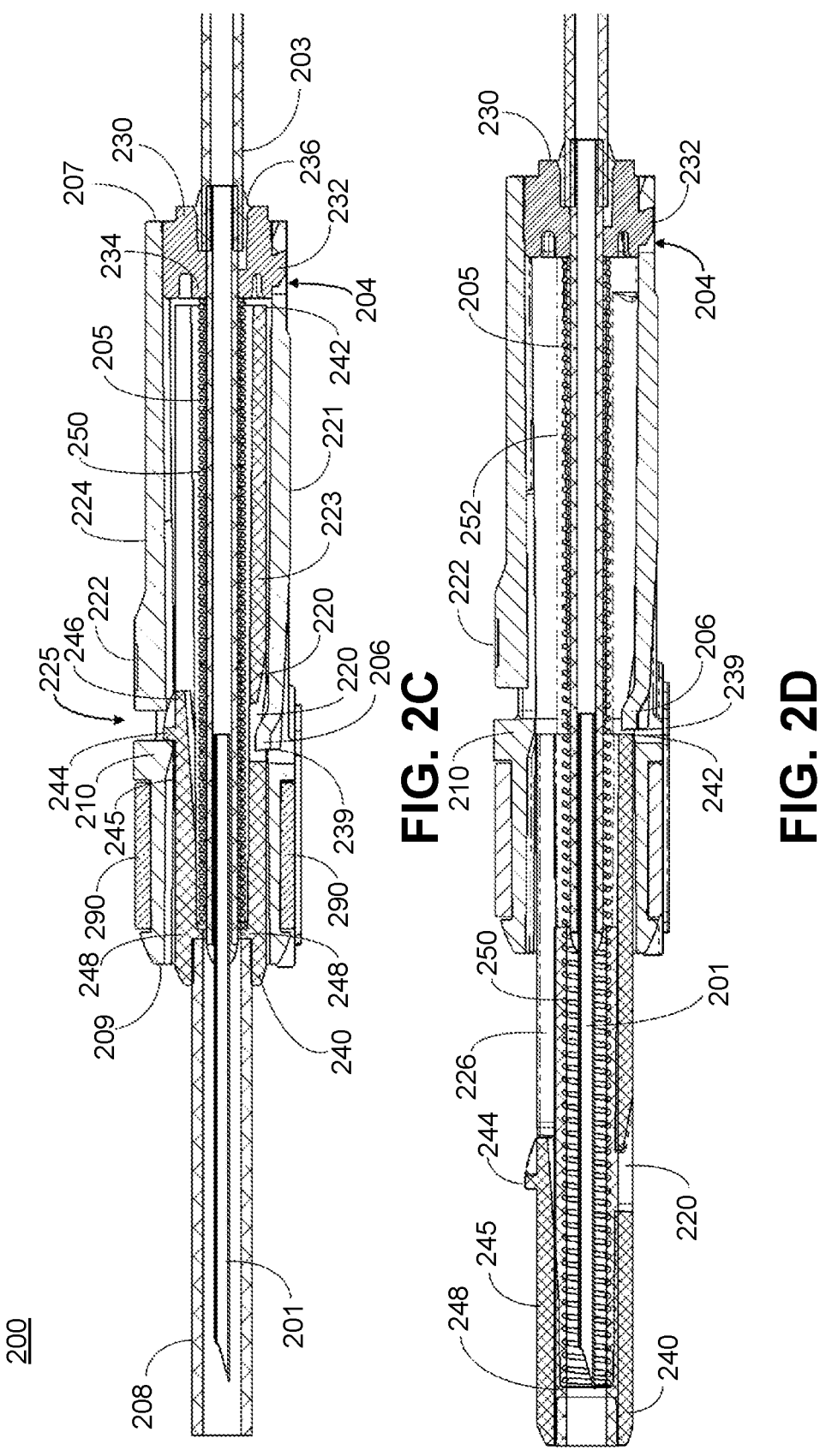

FIGS. 2A and 2B are cross-sectional perspective views of a safety needle assembly 200 in a packaged mode and in a safety mode, respectively, and FIGS. 2C and 2D are vertical cross-sectional side views of the safety needle assembly 200 in the packaged mode and the safety mode, respectively. As shown in FIGS. 2A-2D, a safety needle assembly 200 includes a housing 202, a hub 230 fixed to and housed by the housing 202 and which connects outer tubing 203 (or outer cannula) with inner tubing 205 (or inner cannula), and a needle 201 connected in a fixed position relative to the hub 230 and the housing 202 via the inner tubing 205. In some implementations, the needle 201 can be connected directly to the hub 230. The housing 202, the hub 230, and the shield 240 can be formed of a rigid or semi-rigid material, such as a plastic such as polycarbonate.

The housing 202 can include a groove or indentation on an outer surface to accommodate a collar 290 that is attached to oppositely-extending wings 292, by which a technician can move and manipulate the safety needle assembly 200, and by which the safety needle assembly can be secured to a patient, such as by being taped to the patient's skin proximate a venipuncture, for example.

The safety needle assembly 200 further includes a shield 240 that is initially retracted and locked, against the force of a compressed spring 250, at least partially within the housing 202 so as to expose the needle 201 that extends from a distal end 209 of the housing 202. In the packaged mode, and before use and venipuncture of a patient by the needle 201, the needle 201 can be covered with a removable shroud 208. The shroud 208 can be a measured section of semi-rigid tubing, and can be sized such that the shroud 208 can be inserted into a shroud receptacle or pocket at the face of the shield 240, where the shroud 208 is held in place in the shroud receptacle or pocket by a friction fit, and extend substantially over the distal end and point of the needle 201. When a venipuncture is to occur, the shroud 208 can be removed to expose the needle 201 and discarded.

The shield 240 can be deployed by operation of a shield deployment mechanism, described in further detail below, which, driven by the spring 250 as it releases and expands, deploys, pushes or forces the shield 250 from the packaged mode to the safety mode, in which the shield 250 completely covers the distal end of the needle 201 and shields it from inadvertent needle sticks of a technician, patient or other. The safety needle assembly 200 further includes a shield locking mechanism to lock the shield in the safety mode of the safety needle assembly 200, i.e. where the shield 240 covers the needle 201 and is locked in that position, as described further below.

The hub 230 is fixed at least partially within the housing 202 at a proximal end 207 of the housing 202 opposite a needle 201, and to which outer tubing 203 and inner tubing 205 are connected. The outer tubing 203 can be connected with a fluid collection device and/or a fluid sidelining device, such as a device described in U.S. Patent Publication Nos. 2020/00305780 and 2017/0020427, the contents of which are incorporated by reference herein for all purposes.

The hub 230 can be secured to the housing 202 by a hub flange 232 or catch or post that extends outward from a main body of the hub 230, and which occupies or otherwise connects to or within a housing aperture 204 formed in the housing 202. The hub flange 232 can have an angled forward face and a slightly angled rearward face, as shown in FIGS. 2A and 2B, so as to be easily inserted into the proximal end of the housing 202 during manufacturing, and secured in place in the housing aperture 204 upon insertion of the hub 230 into the housing 202. The angled rearward face prevents the flexible wall of the housing 202 from bending and allowing the hub 230 to be pushed out of or otherwise released from the housing 202.

The hub 230 connects with the outer tubing 203 at an outer or proximal face of the hub 230 at a proximal end 207 of the housing 202. The outer tubing 203 can be positioned inside a cylindrical cavity of the hub 230, as shown in FIGS. 2A and 2B, and/or secured by an adhesive 236. The hub 230 also connects directly with the needle 201 or via an inner tubing 205 on a distal (i.e. needle 201) side, on an inner face. The inner tubing 205 preferably has a similar or smaller internal diameter as the outer tubing 203, which can reduce the risk of hemolysis, for example. The inner tubing 205 is in turn connected and fluidically sealed to the needle 201 within the housing 202, such that the needle 201 extends out of a distal end 209 of the housing 202.

The hub 230 further includes a forward abutment region 234, or distal face, on the inner face of the hub 230, and on which a proximal, or first, end of a spring 250 can abut, be placed or connected, and leveraged against. The spring 250 can be a coiled spring that is coiled, placed or fits around the inner tubing 205 and can be positioned over at least some of the needle 201. In some implementations, the forward abutment region 234 of the hub 230 can be formed as a ring around inner tubing 205, to provide a maximal surface area on which the spring can abut. The forward abutment region 234 of the hub 230 therefore provides an immovable surface against which the spring 250 can release, push, react, or the like.

Packaged Mode—Shield Securement Mechanism

As described above, in the packaged mode, the shield 240 is secured within the housing 202 by a securement mechanism to expose the needle 201, which extends from both the shield 240 and a distal end 209 of the housing 202. The shield securement mechanism can include a lock-in latch 210 as part of the housing 202 that extends into an inner chamber of the housing 202, and which mates with a securement latch 244 as part of the shield 240 proximate a distal end 246 of a flexible and depressible shield securement arm 245, which can also be formed as a cut-out portion of the material the shield 240, as described in further detail below.

The shield 240 can include an abutment member 248, such as inwardly-directed protrusion, near or at a distal end of the shield 240, on which a distal end of the spring 250 can abut, be placed or connected, and leveraged, pushed, or reacted against. The abutment member 248 can be formed by an inward-projecting ring or ridge, and provide an rearward face to abut the distal or second end of the spring 250. The abutment member 248 can also fix or stabilize the needle 201 and/or any associated tubing in a longitudinal position relative to the housing 202. Accordingly, the spring 250 can exert a bias or force against the inner face of the abutment member 248.

In the packaged mode, the lock-in latch 210 of the housing 202 is mated with the securement latch 244 of the shield 240, and the spring 250 is compressed between the forward abutment region 234 of the hub and the abutment member 248 of the shield. The securement latch 244 is latched, pressed, or forced against lock-in latch 210 in the direction of the force of the compressed spring 250, i.e. from the hub toward a distal end 209 of the housing 202 and the needle 201.

Shield Deployment Mechanism

The shield deployment mechanism is implemented by a cooperation between the housing 202, the shield 240 and the spring 250. In some implementations, the housing 202 includes a button 222 for activating a deployment of the shield 240. The button 222 can be a raised portion of a flexible and depressible activation arm 224. The activation arm 224 can be a formed as a cut-out portion of the material that forms the housing 202, as described in further detail below. In some implementations, the housing 202 includes a cut-out space 225 between the button 222 and the lock-in latch 210 to allow space for the securement latch 244 on the securement arm 245 of the shield 240 to extend upward and latch against the lock-in latch 210 of the housing 202.

In some implementations, at least part of the button 222 is positioned above the distal end 246 of the flexible securement arm 245. The distal end 246 forms a platform against which the button 222, when depressed by a technician, pushes the distal end 246 and securement arm 245 down to release the securement latch 244 from abutting against the lock-in latch 210. The distal end 246 can include a downward-sloping shape from the securement latch 244 toward the terminus of the distal end 246, so as to facilitate a smooth and effective disengagement of the securement latch 244 from the lock-in latch 210.

Upon disengagement of the securement latch 244 from the lock-in latch 210, the shield 240 will slide distally away from the hub 230 and out of the distal end 209 of the housing 202, by force of the compressed spring 250 which begins to expand to its original length. The housing 202 can have one or more longitudinal indented grooves 252, channels or tracks, which can extend at least partially along the internal walls of the housing 202, for guiding the sliding and deploying shield 240, which can have corresponding tabs 406 or guides that extend out from an outer surface of the shield 240. Alternatively, the shield 240 can have one or more grooves, channels or tracks 305, while an inner surface of the housing 202 can have corresponding tabs or guides 503. The tracks and guides allow for proper placement and orientation of the shield 240 relative to the housing 202, and where both an inner cross section of the housing 202 and an outer cross section of the shield 240 are circular, can prevent rotation of the shield 240 relative to the housing 202. Further, both an inner cross section of the housing 202 and an outer cross section of the shield 240 can have one or more non-circular shapes, such as an angle or compressed curve, which can also prevent rotation of the shield 240 relative to the housing 202 as the shield 240 is deployed. These tracks and guides, and tabs and guides also cooperate to stop or limit the forward movement of the shield 240 from the housing 202, so that the shield 240 does not become disconnected or eject from the housing 202, as will be described in further detail below.

As the shield 240 slides forward relative to the housing 202 and away from the hub 230, a bottom surface 221 of the shield 240 is configured, by virtue of a ramped front end 223 of the bottom surface 221, to slide over a lock-out latch 206 of the housing 202. The lock-out latch 206 has a forward locking face 239 that is configured to eventually mate against a rear face 242 of the shield 240, such as at the bottom surface 221 of the shield 240, or against tabs that extend out from the shield 240. In the packaged mode, the lock-out latch 206 of the housing 202 protrudes up from an inner surface of the housing to occupy a gap 220 in the shield 240 proximate the ramped front end 223 of the bottom surface 221 of the shield 240.

In some implementations, the outer surface of the shield 240 and the inner surface of the housing, at least at the top and bottom of the shield, are configured to be spaced apart to allow easy deployment of the shield 240 from the housing 202, as well as allow the bottom surface 221 of the shield 240 to slide over the lock-out latch 206, which can be at the end of a cut-out arm formed in the bottom of the housing 202 so as to bend the lock-out latch 206 flexibly out of the way of the bottom surface 221 of the shield 240 as it slides over the lock-out latch 206. This spacing can also allow the securement latch 244 of the shield 240 to slide out of the top inner surface of the housing 202. The shield 240 further includes a channel 226 or groove, opening, or the like, in a surface of the shield 240, such as the top surface, to allow the shield 240 to deploy and slide past the depressed button 222, which can extend at least partially into the channel 226.

The shield 240 will slide forward to deploy over and cover the needle 201. The forward movement of the shield 240 is stopped by a cooperation of the tabs and guides, whether on the inner surface of the housing 202 or outer surface of the shield 240, to stop or limit the forward movement of the shield 240 from the housing 202, so that the shield 240 does not become disconnected or eject from the housing 202, as will be described in further detail below.

Safety Mode—Shield Locking Mechanism

Once the shield 240 has fully deployed in an extended position, i.e. to the maximum extent allowed by the one or more tracks and one or more tabs, the rear face 242 of the bottom surface 221 of the shield 240 moves beyond and forward of or distal to the lock-out latch 208, which returns toward the inner portion of the housing to engage the forward locking face 239 of the lock-out latch 206. Accordingly, the shield 240 cannot be pushed back into or otherwise retracted back inside the housing 202, and the shield 240 will be locked to cover the needle 201. In some implementations, the safety needle assembly 200 is configured such that the spring abutment region 248 of the shield 240, against which the distal end of the spring 250 is attached, extends beyond the distal end or tip of the needle 201, whether or not further coverage by the shield 240 extends further beyond the distal end or tip of the needle 201.

Figure 3:
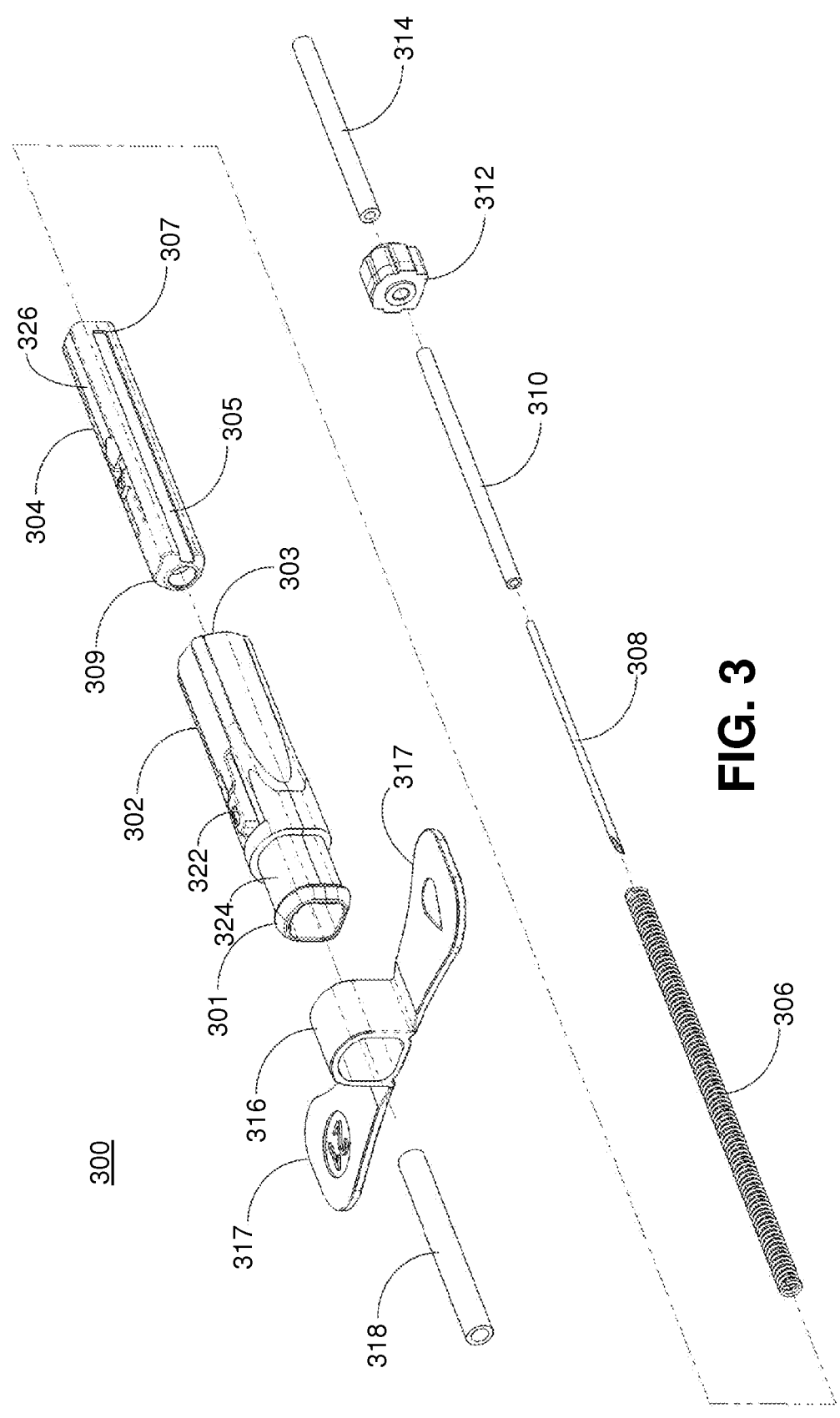
FIG. 3 is an exploded view of a needle assembly in accordance with the implementations described herein.

FIG. 3 is an exploded view of a safety needle assembly 300, particularly illustrating part of a mechanism configured to prevent a shield 304 from ejecting from a housing 302. As shown in FIG. 3, the safety needle assembly 300 includes a housing 302, which can take the shape of an elongated hollow cylinder or semi-circular tube. The elongated shape of the housing 302 aids in housing various other components, as well as provides a surface area by which a technician can grasp or pinch an assembled safety needle assembly 300 and easily control or manipulate it during use. The housing 302 includes a depressible button 322 on an outer surface of the housing 302, which is explained in detail above, and a seat 324 for receiving an elastomeric cuff 316 that includes oppositely projecting wings 317. The wings 317 can be used to control movement and placement of the assembled safety needle assembly 300, as well as provide a surface to anchor the safety needle assembly 300 to a surface, such as the patient's skin or a surface proximate a venipuncture site on the patient.

The shield 304 is inserted into a proximal end 303 of the housing 302 such that a forward face 309 of the shield 304 is at, or slightly extends out from, a distal end 301 of the housing. A shape of an inner surface of the shield 304 corresponds, with some clearance, to the outer surface of the housing 302. In addition, the shield 304 includes one or more channels 305 (groove, indentation, track, etc.) that are inset from an outer surface of the shield 304. The shield 304 includes a releasable securement latch, described in detail above, preferably on a top surface of the shield, and which latches against a corresponding lock-in latch (not shown) in the housing 302 that secures the shield 304 in the housing 302 during assembly at a desired position relative to the housing 302.

Each channel 305 is preferably linear, and preferably extends substantially along the length of the shield 304, but has a terminus 307 proximate or toward a rear face of the shield 304. As such, the channel 305 extends all the way to the forward face 309, to receive a corresponding tab, pin, projection, etc. (not shown) extending out from the inner surface of the housing 302, preferably toward the distal end 302 of the housing 302 such that it occupies a forward part of the channel 305 near the forward face 309 of the shield, as will be illustrated in further detail below. In preferred implementations, the shield 304 includes two channels 305; one channel 305 on opposing side walls of the shield 304.

The shield 304 can include a guide 326 or groove in a surface of the shield 304, such as the top surface, to allow the shield 304 to deploy and slide past the button 322 when depressed, which can extend at least partially into the second channel 326. In some implementation, the guide 326 is a channel or groove, and can also be formed to cooperate with a corresponding rail or ridge that extends inwardly from the housing 302 (not shown), or vice versa.

Figure 4:
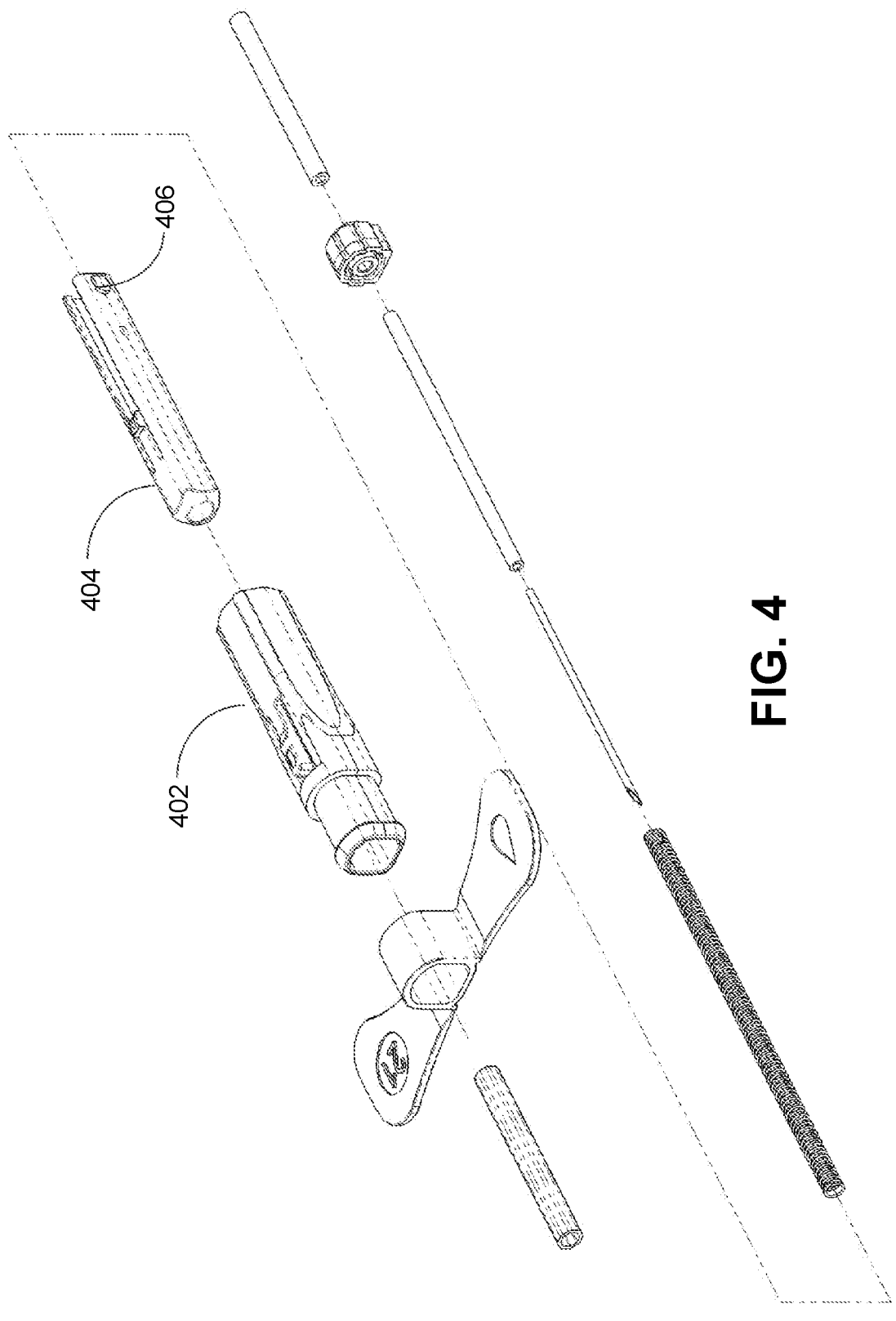
FIG. 4 is an exploded view of a needle assembly in accordance with an alternative implementation.

As described in further detailed further above, as the shield 304 is deployed from the distal end 301 of the housing 302, the tab(s) on the inner surface of the housing 302 will eventually abut or hit up against the terminus 307 of the channel 305 to stop or inhibit any further forward movement or deployment of the shield 304 relative to the housing 302. In alternative implementations, such as shown in FIG. 4, a housing 402 can include one or more channels, and a shield 404 can include one or more tabs 406. In these implementations, each tab 406 protrudes or extends from an outer surface of the shield 404, and can have a shape to correspond at least with a shape of the terminus of the channel in the housing 402. In yet other alternative implementations, each of the housing 302/402 and the shield 304/404 can include at least one channel 305 and at least one tab 406 that corresponds with a channel on the mating component.

The safety needle assembly 300 further includes a spring 306, such as an elongated coil spring in which a needle 308 is inserted. The needle 308 is connected with inner tubing 310. A front end of the spring 306 abuts against a rearward or rear-facing abutment face or region (not shown) near the forward face 309 of the channel, and pushes against the abutment face or region when released to deploy the shield 304 from the housing 302.

The safety needle assembly 300 further includes a hub 312 that is insertable into, and connects with, a proximal end of the housing 302 after insertion and placement of the shield 304 into the housing 302. The hub 312 provides a connecting mechanism to which the inner tubing 310 and outer tubing 314 are connected. The inner tubing 310 extends distally into the shield 304 from the hub 312, while the outer tubing extends proximally out from the hub 312 and the shield 304. The hub 312 also forms or provides a forward or front-facing abutment face or region on which a rear end of the spring 306 abuts, and provides a non-moving platform or anchor against which the compressed spring 306 is released to push the shield 304 out of the housing 302 to deploy the shield 304 over the needle 308.

During assembly, the needle 308 is threaded into and through the spring 306, such that when the hub 312 is connected with the housing 302, the needle 308 extends out from both the shield 304 and the distal end 301 at a length to make venipuncture simple and safe. Upon assembly, and before shipping and use, the needle 308 can be covered and secured by a removable sheath 318, which can be removed before or at time of use, and which can be sized to extend beyond the tip or distal point of the needle 308.

Figure 5A:
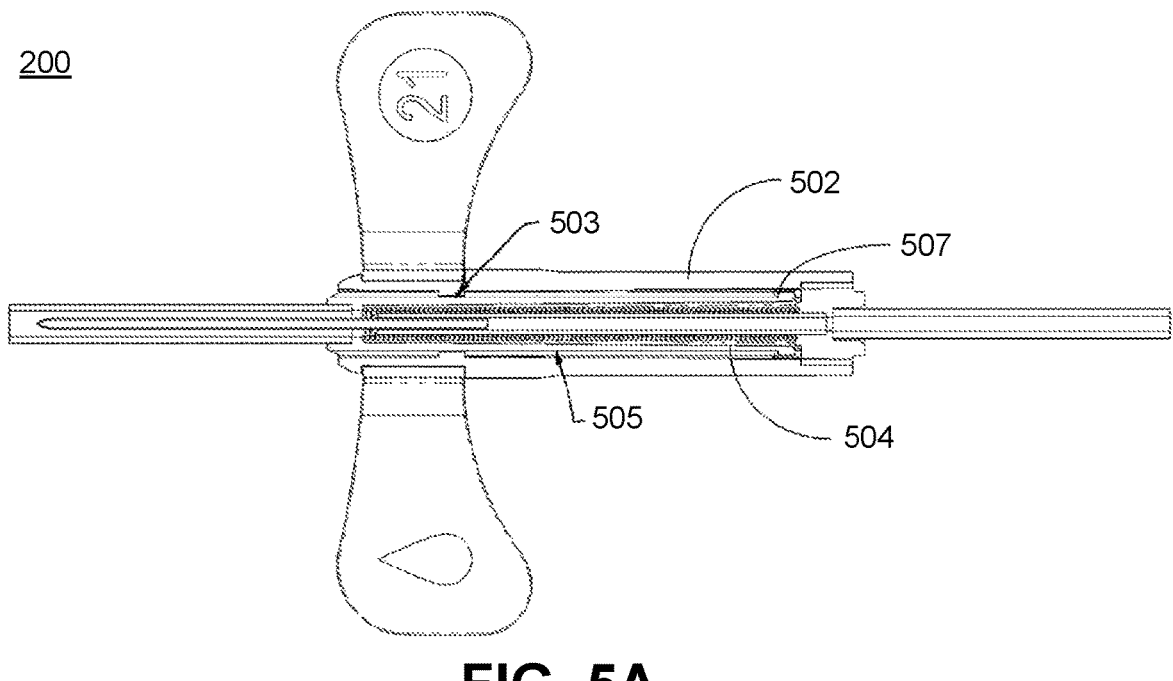
FIGS. 5A and 5B illustrate a safety needle assembly, and in particular a tab and channel mechanism between the housing and shield, respectively.
Figure 5B:
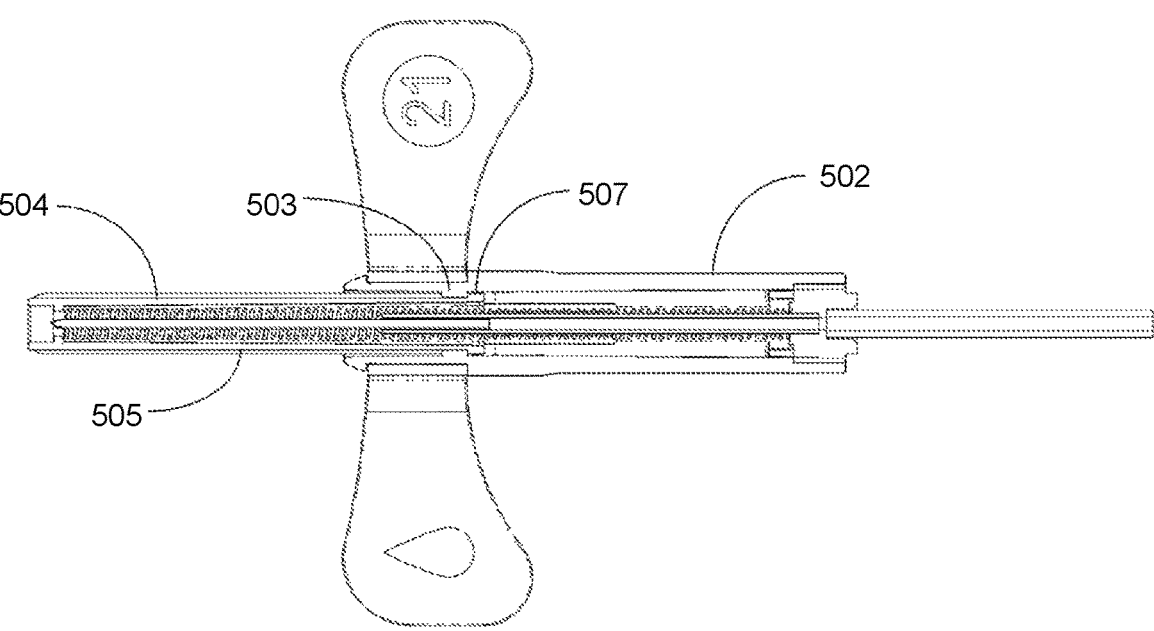

FIGS. 5A and 5B illustrate a horizontal cross section of a safety needle assembly 200, as illustrated in FIGS. 2A-2D, in a ready mode (FIG. 5A) and a safety mode (FIG. 5B), and showing a mechanism configured to prevent a shield 504 from ejecting from a housing 502. The housing 502 includes one or more tabs 503 that protrude or extend from an inner surface of the housing 502. The tabs 503 are preferably positioned toward a forward, or distal, end of the housing 502, as shown in FIGS. 5A and 5B, and are sized and configured for fitting within a corresponding channel 505 or groove, track, etc. formed on an outer surface of the shield 504. The channel 505 extends from a forward face, or front, of the shield 504 and along the length of the shield, until a terminus 507 formed in the outer surface of the shield 504. The terminus 507 can simply be a dead-end of the channel 505 on the shield 504 opposite the forward face.

As shown in FIG. 5B, once the shield 504 is deployed and extended from the housing 502, the tabs 503 of the housing 502 provide a guide within the channel 505 of the shield 504, and eventually abut against the terminus 507 of the channel 505 to thereby prevent or inhibit further movement of the shield 504 relative to the housing 502. At this point, the spring that provides the motive force to the shield 504 is substantially released, yet may still be providing at least some minimal amount of force on the shield 504.

Figures 6A, 6B:
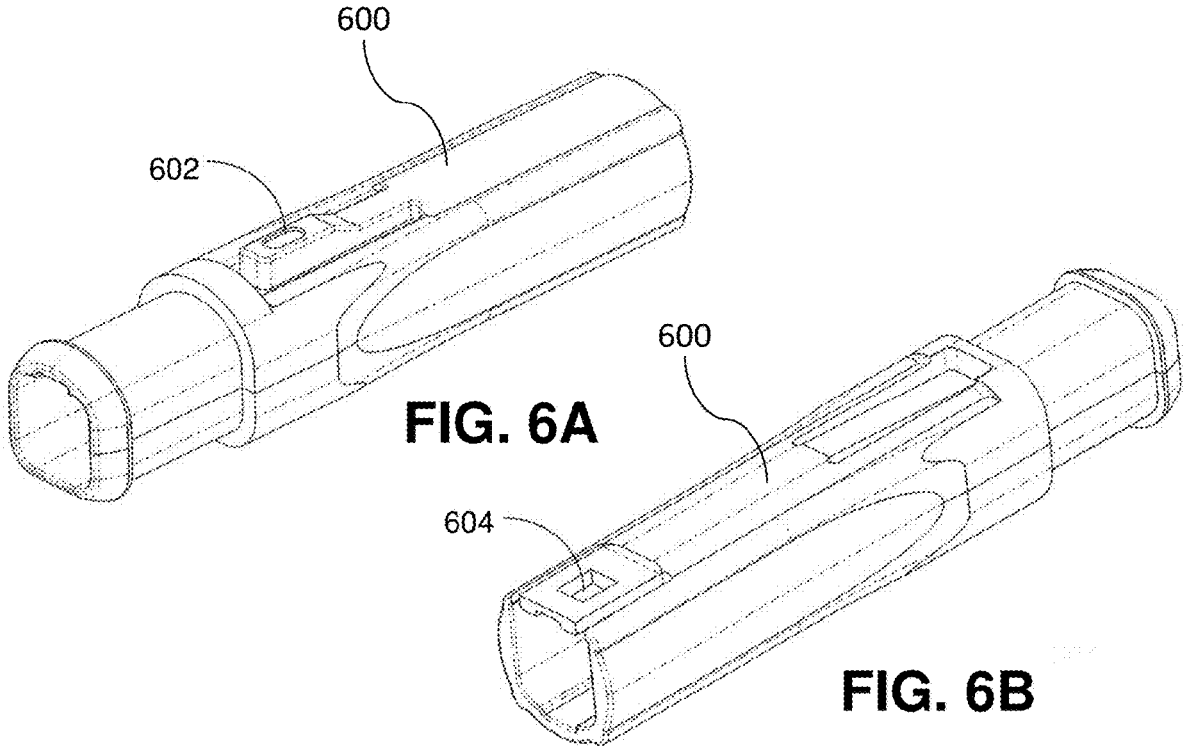
FIGS. 6A-6C show various details of a housing of a safety needle assembly.
Figure 6C:
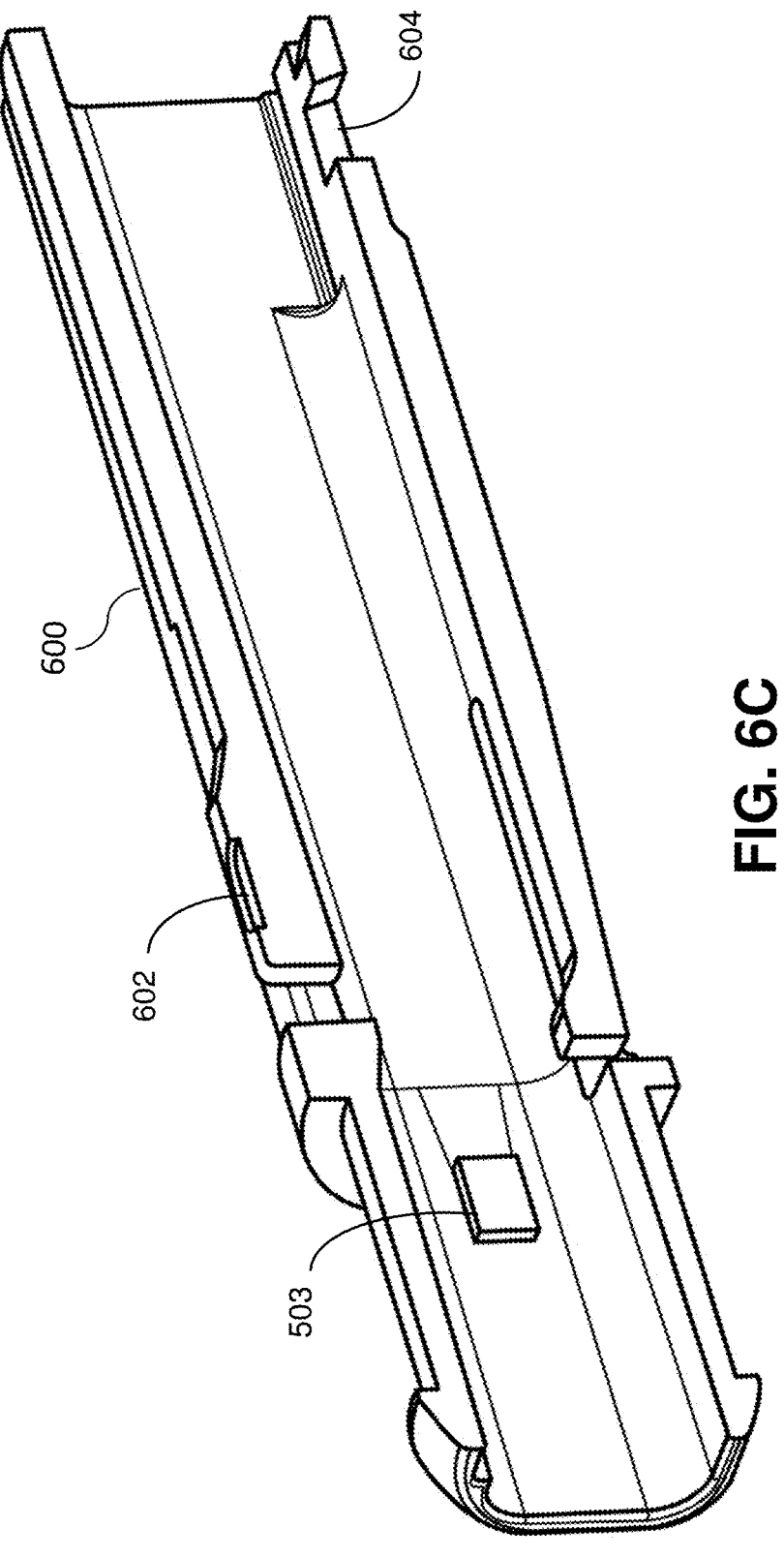

FIGS. 6A-6C show a top perspective view, a bottom perspective view, and a cross-sectional interior view, respectively, of a housing 600 for a safety needle assembly. As can be seen in FIG. A, a top surface of the housing 600 includes a button 602 for releasing a securement latch on a shield from a lock-in latch on an inner surface of the housing 600, as shown and explained in reference to FIGS. 2A-2D. The button 602 is preferably only a single button located on the top surface of the housing 600 so as to be easily seen and accessed by a technician, however, in some alternative implementations, one or more buttons 602 can be located on any part of the outer surface of the housing 600, such as two buttons 602, each being provided on opposing sides of the outer surface of the housing 600.

As shown in FIG. 6B, a bottom surface of the housing 600 includes an aperture 604 that is sized and configured to receive a catch or flange of the hub (not shown), the structure and function of which is described in detail above. The aperture 604 is preferably positioned at a proximal end (i.e. away from a patient) of the housing 600, such that the hub can be easily placed therein for immediate securement.

FIG. 6C is a vertical cross sectional and perspective view of the housing 600, and which shows the tab 503 that extends from the inner surface of the housing 600, as described with reference to FIGS. 5A and 5B. As further described above, the tab 503 is one of one or more tabs that engage with a channel or track on an outer surface of a shield so as to guide deployment and extension of the shield over a needle, as well as to provide a stop to prohibit further deployment and extension of the shield relative to the housing beyond a predetermined length or extent.

Figures 7A, 7B:
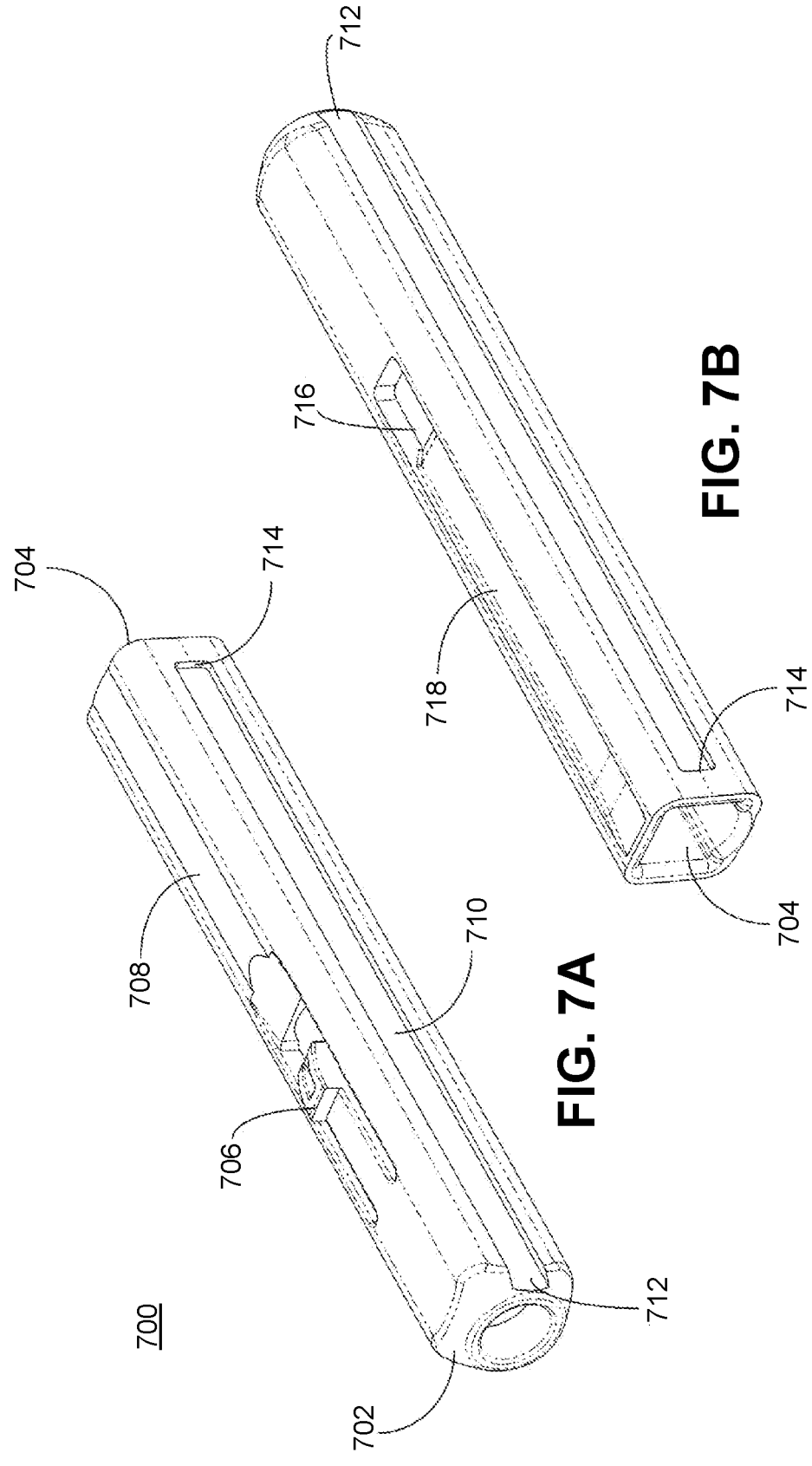
FIGS. 7A and 7B show various details of a shield of a safety needle assembly.

FIGS. 7A and 7B show a top perspective view and a bottom perspective view, respectively, of a shield 700 for a safety needle assembly. The shield 700 has a distal end 702 with an opening through which a needle extends in a packaged mode and during venipuncture, but which extends completely over the needle in a safety mode where the shield 700 is deployed and extended from the housing to cover the needle. The shield 700 further has an opened proximal end 704 for receiving the needle and inner tubing, as well as a spring that is compressed in the packaged mode, as described in further detail above.

As shown in FIG. 7A, the shield 700 includes a securement latch 706 that abuts against and latches with a lock-in latch of the housing, as described above. The shield 700 can also have a groove 708 or channel from proximate the securement latch 706 to the proximal end 704, that enables the shield 700 to slide relative to the housing while not snagging on or being impeded by the housing's depressed button after the securement latch 706 is disengaged from the lock-in latch in a deployment mode.

As shown in FIGS. 7A and 7B, the shield 700 further includes a channel 710 or track that originates as a cut-in 712 at the distal end 702 and ends at a terminus 714 forward of the proximal end 704. The channel 710 receives a tab in the housing, which helps guide deployment and extension of the shield 700 from the housing, and where the tab eventually abuts the terminus 714 of the channel 710 to stop any further extending movement by the shield relative to the housing. Finally, as shown in FIG. 7B, the shield includes a gap 716 for accommodating a flexible lock-out latch of the housing. In alternative implementations, the gap 716 can be followed by a ramped groove 718, having one or more ramped sections, where the gap 716 and groove 718 allow the shield 700 to pass over the lock-out latch as the shield is being deployed, and where the lock-out latch will spring back to an original orientation to engage a face of the proximal end 704.

Figure 8A:
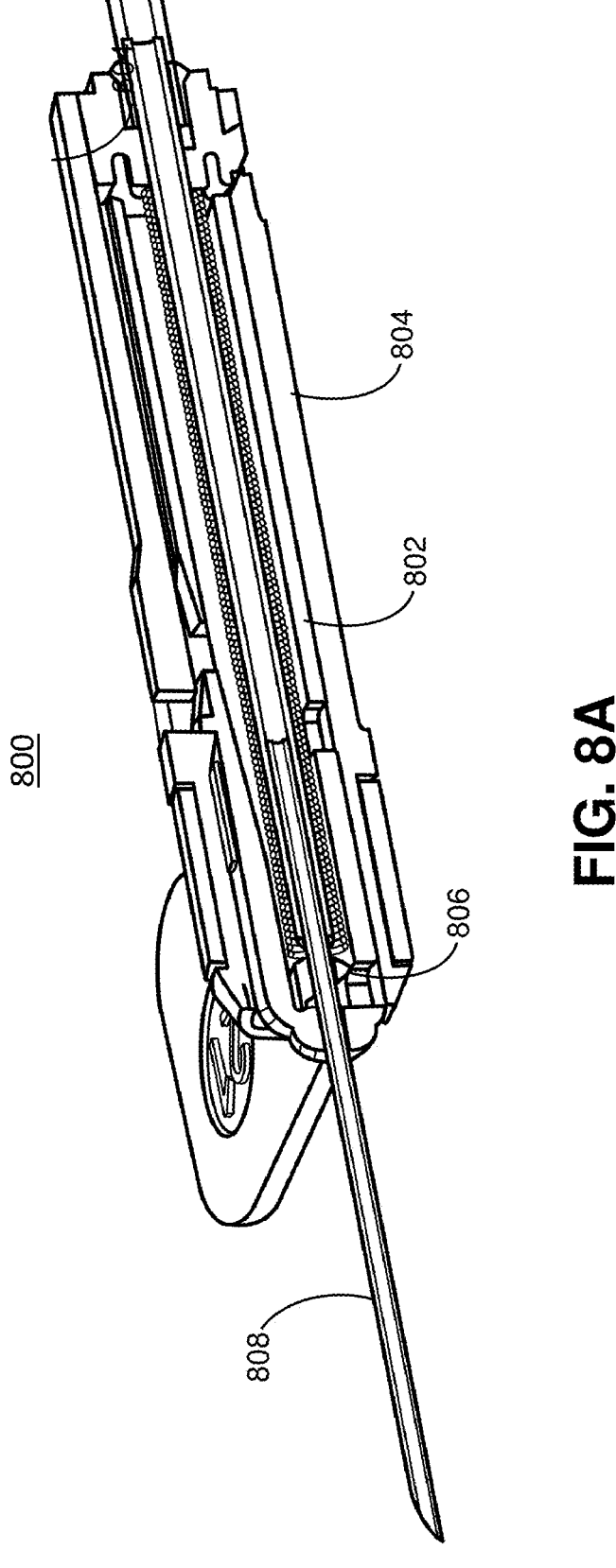
FIGS. 8A-8C illustrate a lock-out mechanism for a safety needle assembly, in accordance with alternative implementations of the subject matter described herein.
Figure 8B:
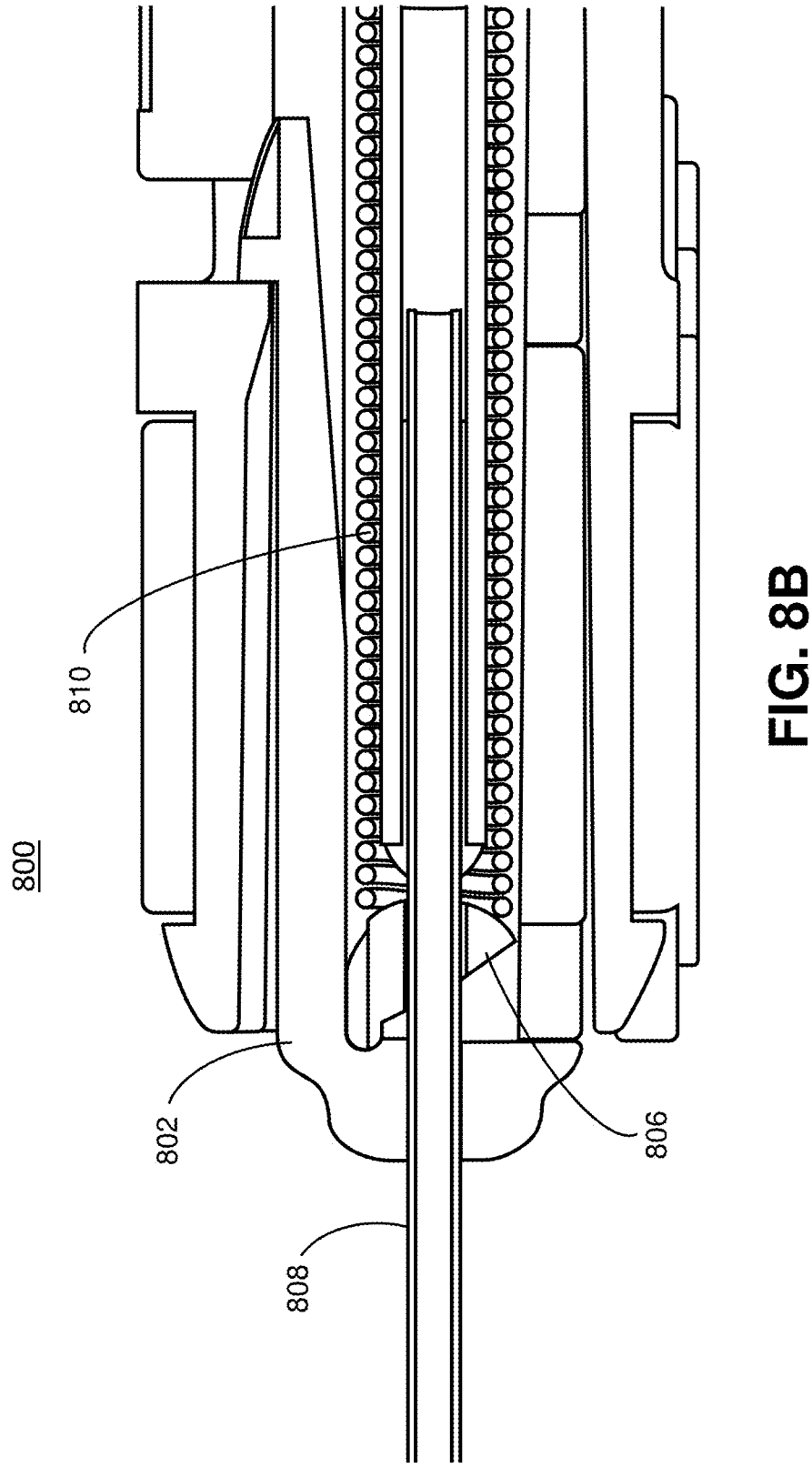
Figure 8C:
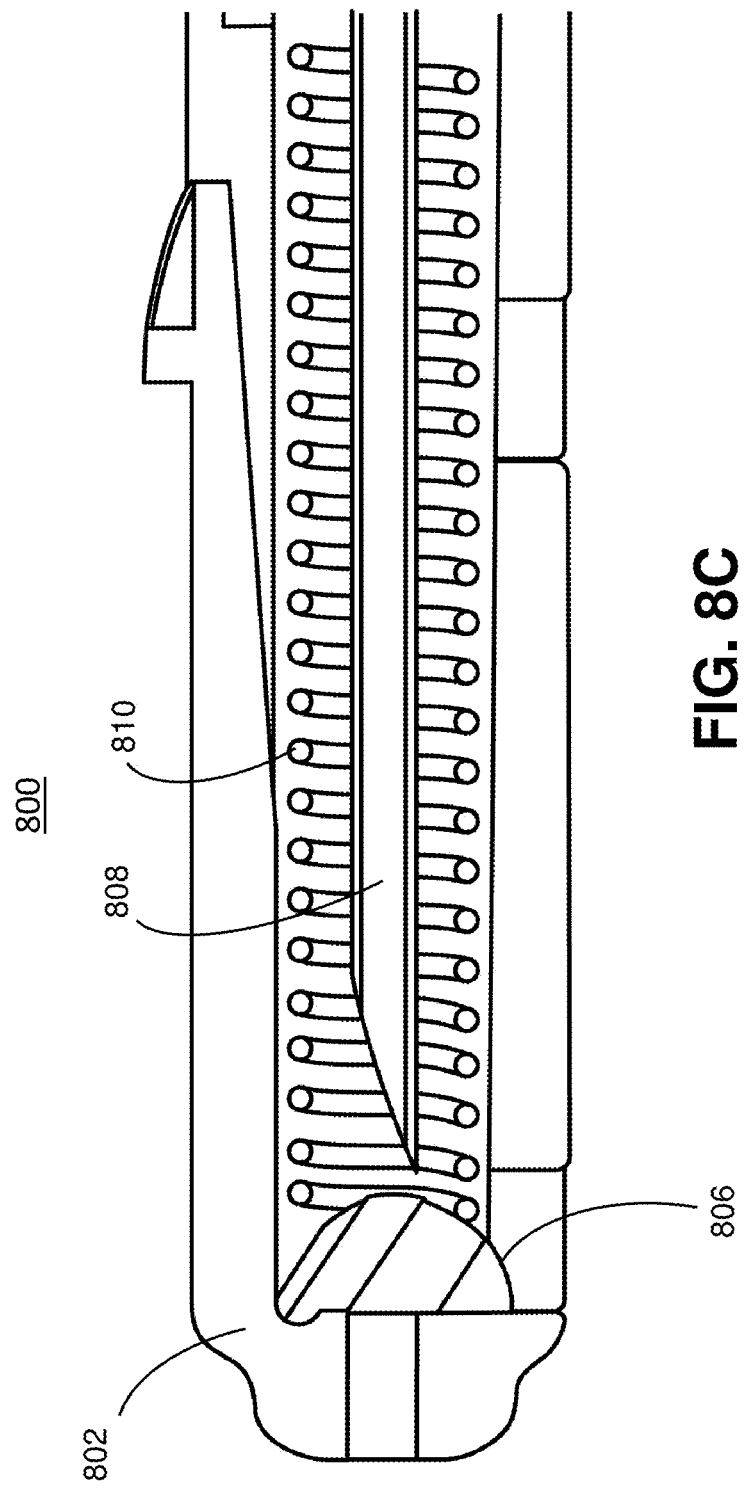

FIGS. 8A-8C illustrate an alternative lock-out mechanism for a safety needle assembly 800, which locks out a shield 802 from a housing 804, or otherwise inhibits or prohibits the shield 802 from being retracted back toward or into the housing 804. While the safety needle assembly 800 is similar to the safety needle assemblies described above, in some implementations, a lock-out mechanism includes a lock-out cylinder 806 that is configured to pivot from an opened position or orientation to a locked-out position or orientation. The lock-out cylinder 806 includes a central hole from a back end to an angled front end, which front end of the lock-out cylinder includes a pivot point at a top portion.

As shown in FIGS. 8A and 8B, in a packaged or in-use mode of the safety needle assembly 800, the lock-out cylinder 806 has a position or orientation such that the central hole aligns with a hole in the forward face of the shield 802, to allow a needle 808 to extend through both the lock-out cylinder 806 and the shield 802. The lock-out cylinder 806 however is biased by spring 810 to pivot downward, while the needle 808 maintains the alignment of the central channel and the shield's 802 hole.

As shown in FIG. 8C, when the shield 802 is deployed and extends over the needle 808, such that the lock-out cylinder 806 is beyond the tip of the needle 808, the spring

810 forces the lock-out cylinder 806 to pivot downward. As such, the central hole of the lock-out cylinder 806 is misaligned from the hole in the face of the shield 802, exposing the tip of the needle 808 to a solid surface of the lock-out cylinder that the needle 808 cannot penetrate or pierce through. Accordingly, the lock-out cylinder 806 will be in the lock-out position or orientation, and thereby using the needle 808 itself as a block to retraction of the shield 802 back to the housing 804.

Although a few embodiments have been described in detail above, other modifications are possible. Other embodiments may be within the scope of the following claims.

The invention claimed is:

1. A safety needle assembly comprising:
a housing having a proximal end, a distal end, and a side wall therebetween which define an inner cavity, the housing including a lock-in latch having a rearward locking face that extends into the inner cavity, and a button formed in the side wall of the housing proximate the lock-in latch, the button being depressible into the inner cavity of the housing, the housing further including a lock-out latch formed in the side wall, the lock-out latch extending into the inner cavity of the housing and having a forward locking face provided on a flexible arm of the side wall of the housing;
a hub fixed within the proximal end of the housing and having an outer face and an inner face, the outer face of the hub being connected with an outer tubing which extends from the hub to outside the proximal end of the housing;
a needle connected with the inner face of the hub to extend at least partially from the distal end of the housing in a fixed longitudinal position relative to the housing;
a spring having a first end and a second end, the first end of the spring abutting the inner face of the hub; and
a shield provided in the inner cavity of the housing, the shield having a proximal end and a distal end, the shield having an abutment member proximate the distal end of the shield and abutting the second end of the spring, the shield further having a securement latch that is configured to latch with the lock-in latch of the housing in a first mode in which the shield is retracted into the housing to expose the needle, and to disengage with the lock-in latch when the button is depressed into the inner cavity of the housing in a deployment mode in which the shield extends out of the housing to cover the needle, the shield further having a bottom groove to bend away the flexible arm of the side wall of the housing to allow the shield to slide by the flexible arm, and to return the flexible arm such that the forward locking face of the lock-out latch engages the proximal end of the shield to inhibit retraction of the shield.

2. The safety needle assembly in accordance with claim 1, wherein the button is formed in a top of the housing as a cutout of the side wall.

3. The safety needle assembly in accordance with claim 2, wherein a top of the button is raised from a top surface of the side wall, and wherein the top of the button includes one or more ridges.

4. The safety needle assembly in accordance with claim 1, wherein the lock-out latch is positioned in a bottom of the housing opposite the button.

5. The safety needle assembly in accordance with claim 1, wherein the needle is connected with the hub via an inner tubing.

6. The safety needle assembly in accordance with claim 1, wherein the abutment member is a ridge protruding inwardly from an inner surface of the shield.

7. The safety needle assembly in accordance with claim 6, wherein the ridge includes an inward abutment face.

8. A safety needle assembly comprising:

a housing defining an inner cavity, the housing including a lock-in latch having a rearward locking face that extends into the inner cavity, and a button formed in a side wall of the housing proximate the lock-in latch, the button being depressible into the inner cavity, the housing further including a lock-out latch formed in the side wall, the lock-out latch extending into the inner cavity and having a forward locking face provided on a flexible arm of the side wall of the housing;

a hub fixed within the housing and having a proximal face and a distal face, the proximal face being connected with an outer tubing that extends outside a proximal end of the housing, the distal face being connected with a needle that extends at least partially out from a distal end of the housing;

a spring having a first end and a second end, the first end of the spring abutting the distal face of the hub; and a shield provided in the inner cavity of the housing and having a proximal end of the shield and a distal end of the shield, the shield having an abutment member proximate the distal end of the shield and abutting the second end of the spring, the shield further having a securement latch that is configured to latch with the lock-in latch of the housing in a first mode in which the shield is retracted into the housing to expose the needle, and to disengage with the lock-in latch when the button is depressed into the inner cavity of the housing to unlatch the securement latch from the lock-in latch in a deployment mode in which the shield is extended out of the housing to cover the needle, the shield further configured to bend away the flexible arm of the side wall of the housing to allow the shield to slide by the flexible arm, and to return the flexible arm such that the forward locking face of the lock-out latch engages the proximal end of the shield to inhibit retraction of the shield.

9. The safety needle assembly in accordance with claim 8, wherein the abutment member of the shield is sized and configured to maintain the needle in a fixed position relative to the housing.

10. The safety needle assembly in accordance with claim 8, wherein the button is formed as a cutout in a top of the side wall of the housing.

11. The safety needle assembly in accordance with claim 10, wherein a top of the button is raised from a top surface of the side wall, and wherein the top of the button includes one or more ridges.

12. The safety needle assembly in accordance with claim 8, wherein the lock-out latch is positioned in a bottom of the housing opposite the button.

13. The safety needle assembly in accordance with claim 8, wherein the needle is connected with the hub via an inner tubing.

14. The safety needle assembly in accordance with claim 8, wherein the abutment member is a ridge protruding inwardly from an inner surface of the shield.

15. The safety needle assembly in accordance with claim 14, wherein the ridge includes an inward abutment face.

16. A safety needle assembly comprising a housing defining an inner cavity and having a depressible button;

a hub positioned in the inner cavity at a proximal end of the housing;

a needle connected with a distal face of the hub to extend out of a distal end of the housing;

a shield positioned in the inner cavity and around the needle, the shield having a retracted mode in which the shield is retracted into the housing to expose the needle out of the distal end of the housing, and a securement mode in which the shield is extended over a distal end of the needle to cover the needle;

a spring connected between the hub and the shield and configured to transition the shield from the retracted mode to the securement mode;

a lock-in mechanism configured to releasably maintain the shield in the retracted mode, the lock-in mechanism comprising a lock-in latch formed in the housing proximate the depressible button and having a rearward locking face that extends into the inner cavity, and a securement latch formed on the shield and configured to latch with the lock-in latch in the retracted mode, when the depressible button is depressed the securement latch is configured to unlatch from the lock-in latch to activate the spring to extend the shield to transition the shield from the retracted mode to the securement mode; and a lock-out mechanism configured to securely maintain the shield in the securement mode, the lock-out mechanism comprising a lock-out latch extending into the inner cavity from a flexible arm of the housing, the lock-out latch configured to abut a proximal end of the shield when the shield is deployed in the securement mode.

17. The safety needle assembly in accordance with claim 16, wherein the depressible button is formed as a cutout in a side wall between the proximal end of the housing and the distal end of the housing.

18. The safety needle assembly in accordance with claim 16, wherein the lock-out latch is positioned in a bottom of the housing opposite the depressible button.

19. The safety needle assembly in accordance with claim 16, wherein the shield includes an abutment member extending inwardly to connect with the spring.

20. The safety needle assembly in accordance with claim 19, wherein the abutment member is sized and configured to maintain the needle in a fixed position relative to the housing.

* * * * *